(12) United States Patent
Ritsche

(10) Patent No.: US 6,461,322 B1
(45) Date of Patent: Oct. 8, 2002

(54) MEDIA DISPENSER

(75) Inventor: Stefan Ritsche, Radolfzell (DE)

(73) Assignee: Ing. Erich Pfeiffer GmbH, Radolfzell (DE)

( * ) Notice: Subject to any disclaimer, the term of this patent is extended or adjusted under 35 U.S.C. 154(b) by 142 days.

(21) Appl. No.: 09/651,700

(22) Filed: Aug. 30, 2000

(30) Foreign Application Priority Data

Sep. 8, 1999 (DE) .......................... 199 42 791

(51) Int. Cl.⁷ .................. A61M 31/00; A61M 13/00; A61M 5/00; A61M 11/00
(52) U.S. Cl. ............... 604/57; 604/58; 604/59; 604/62; 604/187; 128/200.22
(58) Field of Search ................ 604/57, 58, 59, 604/62, 187; 128/200.22

(56) References Cited

U.S. PATENT DOCUMENTS

| | | | | |
|---|---|---|---|---|
| 5,224,471 A | * | 7/1993 | Marelli et al. | 128/200.14 |
| 5,262,142 A | | 11/1993 | Koga et al. | 423/328.1 |
| 5,284,132 A | | 2/1994 | Geier | 128/200 |
| 5,289,818 A | * | 3/1994 | Citterio et al. | 128/200.14 |
| 5,323,936 A | * | 6/1994 | Wolter et al. | 222/401 |
| 5,366,122 A | * | 11/1994 | Guentert et al. | 128/200.22 |
| 5,380,504 A | | 1/1995 | Lindquist et al. | 423/23 |
| 5,431,155 A | * | 7/1995 | Marelli | 128/200.14 |
| 5,683,361 A | * | 11/1997 | Elk et al. | 222/82 |
| 5,984,897 A | * | 11/1999 | Petersen et al. | 604/187 |
| 6,105,823 A | * | 8/2000 | Seager et al. | 222/137 |

FOREIGN PATENT DOCUMENTS

| | | |
|---|---|---|
| DE | 40 15 367 A1 | 5/1990 |
| DE | 41 28 295 A1 | 8/1991 |
| DE | 691 23 357 T2 | 3/1992 |
| DE | 195 25 734 A1 | 7/1995 |
| DE | 196 47 947 A1 | 11/1996 |
| DE | 197 00 437 A1 | 1/1997 |
| DE | 197 04 849 A1 | 2/1997 |
| DE | 197 11 791 A1 | 3/1997 |
| DE | 19750872 | 5/1999 |
| EP | 0 473 965 B1 | 8/1991 |
| EP | 0 680 768 B1 | 8/1991 |
| WO | 97/41831 | 11/1997 |
| WO | 99/31952 | 7/1999 |

* cited by examiner

Primary Examiner—William C. Doerrler
Assistant Examiner—Filip Zec
(74) Attorney, Agent, or Firm—Quarles & Brady LLP

(57) ABSTRACT

The nasal dispenser (1) consists of but two integral housing bodies (4, 5) for accommodating a medium blister (6). Bodies (4, 5) are interlocked by withdrawal prevention means against separation and by releasable blocking means (49) against actuation. The medium reservoir (7) is located freely in an innermost housing space (62) of the first housing body (4). Thus the dispenser (1) is highly compact, simple in configuration and permits facilitated handling.

31 Claims, 1 Drawing Sheet

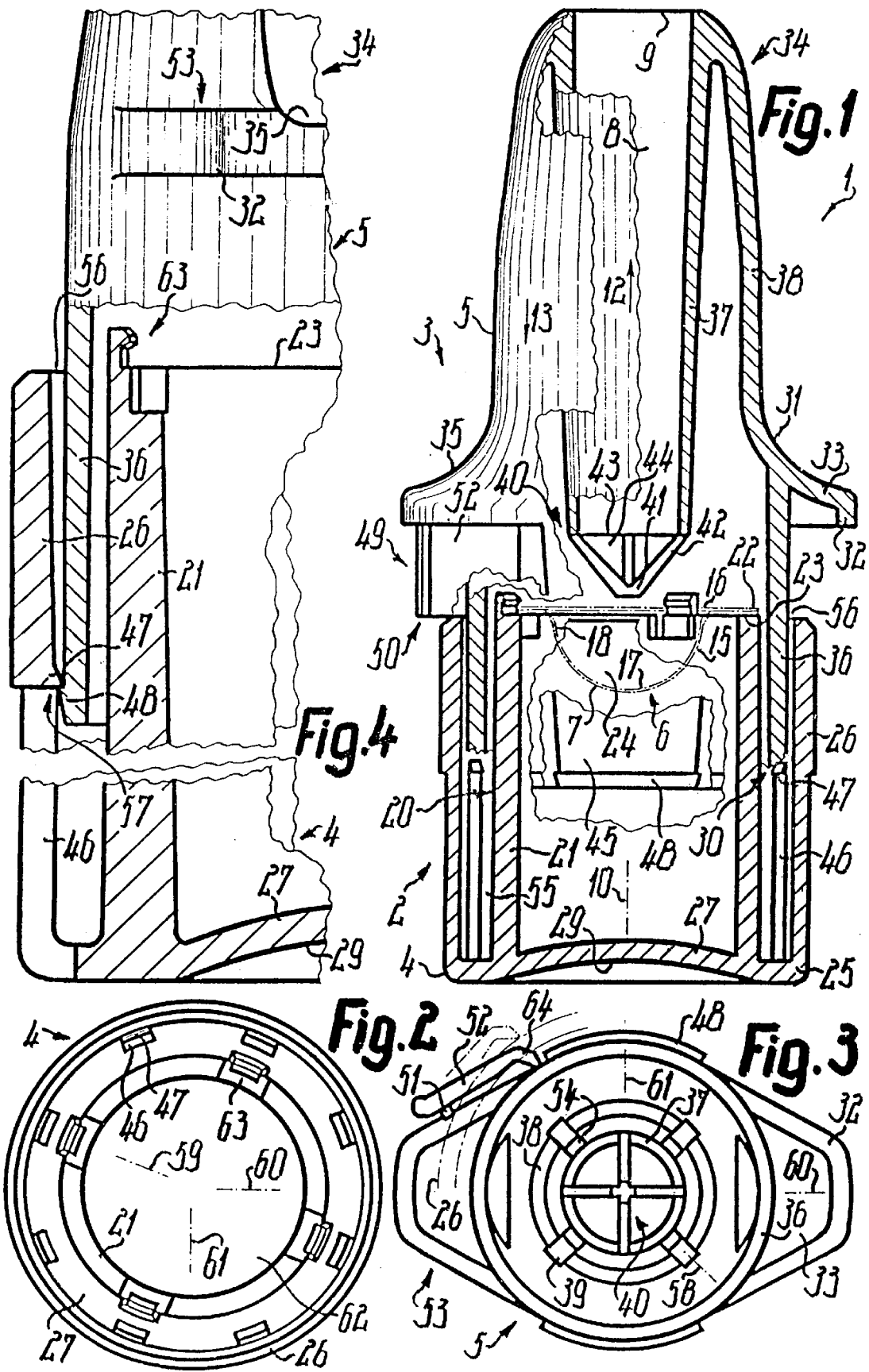

MEDIA DISPENSER

TECHNICAL FIELD AND BACKGROUND OF THE INVENTION

The invention relates to a dispenser for liquid, gaseous, solid or preferably powdery media. The dispenser permits to be held and simultaneously actuated for discharge single-handedly. Furthermore, some or all of its components are partly or entirely fabricated from plastics or injection molding. The flowable medium may be conveyed by suction or inhalation. Thus the pharmaceutical active substance is inhaled or deposited on the nasal mucuous membrane.

OBJECTS OF THE INVENTION

An object of the invention is to avoid the drawbacks of known configurations. Another object is to provide a dispenser which is highly compact and of simple structure. A further object is to make the dispenser very handy and convenient to actuate. Still another object is to prevent inadvertent actuation and damage of the dispenser by axial or radial compressive stress. A still further object is to have the weight of the dispenser very low. Another object is to permit modest manufacture and assembly of the dispenser.

SUMMARY OF THE INVENTION

According to the invention an outer guide shell freely protruding in the flow direction is readily accessible from without and serves to guide the downstream or second dispenser unit which may have a runner shell sliding on the inside of said guide shell. Where the runner shell directly engage sbetween two codirectional guide shells, these may instead freely protrude counter the flow direction and be provided on the second dispenser unit. Thus highly precise guidance and a labyrinth-type sealed closure of the dispenses inner space is achieved by these housing shells. In addition, catch members for blocking may be protectedly located between the guide shells or in the gap between a guide shell and the runner shell.

The reception or hold for the reservoir may be located totally within a shell into which the reservoir tray or dish then protrudes without contact. All three housing shells may thus permanently entirely surround the reservoir chamber and protect this chamber from deformation due to compressive stress from without. The catch action may prevent the units from being pulled apart and separated axially or from being mutually twisted. Thereby withdrawal may be facilitated in overcoming a snap-action force in one rotary position but prevented in another rotary position even against considerably higher withdrawal forces or made possible only by destruction. The first or the second unit may be centrically symmetric in all cross-sections.

Deviating therefrom the second unit may comprise transverse lugs directed away from each other. These lugs protrude as sole portions of the second unit radially beyond the outer circumference of the first unit and each serve as an actuating handle for resting a users finger during manual operation of the dispenser, namely in shortening it. The runner shell may directly and integrally adjoin the inside of these lugs and form a slightly widened continuation of an outermost stud shell of the second unit. An inner stud shell is located within the outer stud shell and may form a spike for opening the reservoir closure on the working stroke. The slimmer stud shell bounds the outlet duct. Both stud shells commonly bound the medium outlet.

The dispenser may consist of but two components, each of which is in one piece, and into which merely the reservoir, for example a blister, needs to be inserted. Releasable blocking means for preventing accidental actuation may be in one part with one of these units while blocking the other unit by abutting on an end face. The locking member is either turned or torn off to release actuation of the working stroke. A suitably high axial actuation force for the working stroke may also release the locking member and thus result in a high actuating tension on commencement of the working stroke.

The dispenser is particularly suitable for discharging biological active substances, such as biochemical expedients or remedies capable of controlling or supporting the medicinal effect of pharmaceutical active substances, e.g. by delaying release of the drug, by improving resorption or the like without it itself needing to have a direct pharmacological effect. The substances may also be peptides, proteins and or hormones, e.g. steroid hormones, polypeptide or proteo hormones or releasing hormones. Examples are oxytocin, vasopressin, insulin, glucagon, parathormon, calcitonin, thyroid hormones, catechol amines, acetylcholine, prostaglandins or the like. In addition the dispenser is suitable for discharging adjuvants such as a Freund adjuvant which when applied in conjunction with an antigen non-specifically amplifies the response of the patients immune system or alters the nature of the immune response and may contain aluminum compounds, mineral oils or inactivated mycobacteria. Such pharmacokinetic drugs may also enhance the effect of some other medicine.

BRIEF DESCRIPTION OF THE DRAWINGS

Example embodiments of the invention are explained in more detail in the following and illustrated in the drawings in which:

FIG. 1 is a partially cross-sectional view of a dispenser according to the invention, FIG. 2 is a plan view of the first unit of the dispenser of FIG. 1, FIG. 3 is a view from underneath of the second unit, and FIG. 4 is a detail taken from FIG. 1 but in a turned magnified view.

DETAILED DESCRIPTION

FIG. 1 illustrates the dispenser 1 in the rest position with a length of max. 70 mm or 55 mm and a diametral extension of its two units 2, 3 only half as large at the most. By a working stroke units 2, 3 are translated into an actuated end position with shortening of the dispenser but without being twisted relative to each other. Units 2, 3 may be twisted relative to each other by more or less than 360° without simultaneous change in length. Units 2, 3 may be locked on each other to prevent rotation. First unit 2 consists exclusively of an integral first base body 2 as well as, where necessary, a reservoir body 6 inserted therein. Second unit 3 consists exclusively of an integral second base body 5, the overall length of which amounts to at least three fifths of the dispenser length 1. The dispenser 1 serves to accommodate a single medium dose and is suitable for recycling after delivery thereof. The medium dose is considerably smaller than the reservoir volume. On delivery the medium flows through reservoir 7 directly into a straight outlet duct 8 out of the end or medium outlet 9 of duct 8. The diameter of outlet 9 is more than 3 mm or 5 mm. All of the cited parts are permanently located in a common dispenser axis 10 to which the discharge direction 12 and the opposing actuating direction 13 are parallel. Outlet 9 may also be an atomizing nozzle.

Reservoir 7 has a reservoir dish or tray 15, the flat dish rim of which is hermetically sealed by a reservoir closure 16 such as a flat diaphragm, film or foil. The semispherical dish bottom 17 translates into a reservoir shell 18 adjoining a flat, annular reservoir rim 22.

Reservoir body 6 has no breakthroughs and is located totally within the supporting body 20 of unit 2. Bodies 4, 5 comprise housing shells 21, 26, 36, namely two guide shells 21, 26 on body 4 and a runner shell 36 inbetween on base body 5. The inner guide shell 21 forms the supporting body 20 on the free end face or shoulder 23 of which the flexibly bendable or elastic rim 22 is supported.

Body 4 is a cap longer relative to its diameter. The outermost and readily accessible shell of body 4 is the outer guide shell 26. Both shells 21, 22 freely protrude from an end wall 27 in direction 12. The centrically recessed outside of wall 27 forms an actuating handle 29. Dish 15 is located within shell 21 with radial spacing and without walls 17, 18 being additionally supported. Shoulder 23 slightly protrudes beyond shell 26.

On insertion of body 6 a positive lock becomes effective. This lock has resilient snap projections protruding beyond shoulder 23 and urging rim 22 against shoulder 23 without reservoir body 6 being positively locked against being twisted.

Shells 21, 26, 36 form the sole interconnection 30 of bodies 4, 5. Connection 30 is totally covered from without. Body 5 too is a cap symmetrical to two mutually perpendicular axial planes 60, 61. Body 5 has its largest radial extension in plane 60. Cap shell 36 freely protrudes beyond end wall 33 in direction 13 and has a thickness greater than half the spacing between shells 21, 26. Thus shell 36 is simultaneously or optionally slidingly guided at both shells 21, 26. The free end face of shell 26 abuts on the free end of an outer shell or shield jacket 32 at the end of the stroke. Jacket 32 protrudes from end wall 33 radially outside of shell 36 in direction 13.

In this end position passages 55 are open between the circumferential and opposed faces of shell shells 21, 26, 36. Passages 55 form suction ducts for ambient air. These ducts define labyrinthine counterdirected flow directions and extend over the full circumference of bodies 4, 5. Inlet openings 56 may be located at the free end of guide shell 26 and may be annular or formed by breakthroughs or recesses 46 in the shell 26. The air flows between shells 21, 36 in direction 12 toward the plate-shaped rim 22, from there radially to axis 10 and then in direction 13 into chamber 24, from where it, in entraining the medium, flows back in direction 13 to directly emerge from the outlet 9. By manually covering suction openings 46, the air flow can be variably throttled for the same suction performance.

Shells 32, 36 and end wall 33 translate in direction 12 into a freely protruding outlet or insertion stud 34. On both sides of plane 60 the outer stud shell 38, 34 translates shoulderless directly into runner shell 36 (FIG. 4). On both sides of plane 61 shell 38 translates into end wall 33 and then into outer shell 32. Wall 33 and jacket 32 extend only over part of the dispenser circumference. Thus two transverse lugs 53 protrude radially outwardly and commonly with outer shell 32 form the radial outermost portions of dispenser 1. The outsides of transition walls 33 thus form concave actuating handles 35 located radially outside of handle 29. In the end position shell 36 is spaced from bottom or end wall 27.

Closing or assembling housing 25, 31 simply requires shell 36 to be introduced between shells 21, 26 in direction 13 without bodies 5, 6 coming into mutual contact. Stud 34 comprises an inner stud shell or spike 37 radially spaced from and located within outer stud shell 38. Shell 37 protrudes beyond shell 32 in direction 13 but is set back by more than its diameter relative to the free end of shell 36. The downstream ends of shells 37, 38 translate with an annular zone integrally into each other. There they bound outlet 9. Shell 37 bounds duct 8. On the outer circumference tube or shell 37 may comprise ribs 39 located in axial planes 58 assuming an angle of 45° to planes 60, 61. Ribs 39 do not adjoin shell 38.

For opening the film or foil 16 the end of shell 37 is a conical tool 40 having a blunt tip 41 translating into diverging webs 42 which are located in planes 60, 61. Between these parting webs 42 in each case an opening of a passage inlet 43 is located.

Shell 36 or shell 26 forms a radially yielding spring 45 to enable cams or counter stops 48 of body 5 to be brought into engagement with stops 47 of body 4. Stops or catch members 47 form means for preventing withdrawal at the downstream ends of axial slots or recesses 46. Recesses 46 traverse wall 27 between shells 21, 26. Eight stops 47 are interspaced by arc angles larger than their own arc angle extension about axis 10. The two counter stops 48 are located symmetrical to plane 61 on both sides of the plane 60. Each stop 48 has an arc exension about axis 10 which is so large that the individual stop 48 can engage only two stops 47.

When stop 48 is oriented rotationally symmetrical to these two stops 47 the body 5 is withdrawable from body 4 possibly only by great exertion of a very high force or by destruction of body 4. When stop 48 is oriented symmetrical to a sole stop 47 this force is substantially less to permit non-destructive opening of housing 24, 31. Counter stops or second snap members 48 connect to the free end of shell 36 and form resilient snap cams which initially override the stops or first snap members 47 on assembly. Stops 47 protrude beyond the inner circumference of shell 46 and stops 48 beyond the outer circumference of shell 36.

Counter stops 48 may also engage slots 46 to thus form a lock positively preventing mutual rotation of bodies 4, 5. In rest position stops 47 and 48 are in mutual contact for positively preventing withdrawal. Reservoir body 6 too is releasable from support 63 after separation of bodies 4, 5.

To thwart tampering and also to prevent accidental actuation blocking means 49 are provided for the rest position. While active these means permit separation and also mutual twisting of housing bodies 4, 5. As evident from FIG. 3 the sole locking member 52 is in contact with the outside of a flank of only one of the trapezoidal lugs 53. Member 52 integrally adjoins via a nominal breaking element 51 or a hinge the end face of shell 32 of this lug 53.

Locking member 52 thus forms a spacer which contacts the end face of shell 26 only at a spacing from element 51. Member 52 is supported relative to body 5 only by element 51. Member 52 is a two-armed lever. The arm remote from shell 26 can be depressed so that its locking arm as evident from FIG. 3 can be pivoted out of the motion range of shell 26. The free end of the locking arm forms a finger rest or handle 64 and may contact the outer circumference of shell 36 so that it can be undergrasped by a finger and withdrawn from the vicinity of shell 26. On sufficiently far swivelling element 51 may also shear off to enable member 52 to be totally separated from dispenser 1. Member 52 may, however, also slide on shell 36 during the working stroke.

Furthermore, member 52 is arranged so that its element 51 tears under an accordingly high axial load excerted by shell 26 to thus overcome blocking means 59. Thus a pressure or trigger point control 50 is created which requires the increased pressure load until element 51 is overcome whereafter control 50 abruptly permits considerably more easy shifting of bodies 4, 5. This may be practical not only for quickly opening closure 16 but also for conveying the medium out of chamber 24 by a pump actuated by the axial motion. On the working or opening stroke the tip 41 pricks closure 16, whereafter rib 39 further slits open closure 16 up to shell 18 by its end edges 54. Then tip 41 may press bottom 17 slightly downwards to give chamber 24 a more favorable shape for the discharge flow.

The four locking members of support 63 are located in axial planes 59 displaced relative to planes 58, 60, 61 about axis 10. In each of planes 59 two stops 47 and recesses 46 are located.

When, after closure 16 has been opened, stud 34 is introduced into a nostril the air can be inhaled valvelessly from inlet 46, 56 up to outlet 9 into the nose. This air entrains the medium from chamber 24 onwards.

The flank webs of shield jacket 32 of each lug 53 diverge at an acute angle with plane 61 and translate tangentially into shell 36. Thus these webs form no shield jacket in the vicinity of plane 61 or as shown in FIG. 3 in the vicinity of stops 48, whilst lugs 53 cover shell 26 or the entire body 4. As evident from FIG. 3 body 4 or guide shell 26 protrudes beyond the outer circumference of body 5 only between lugs 53 or in the vicinity of stops 48, whilst lugs 53 cover shell 26 or the entire body 4.

In another embodiment of the dispenser, e.g. including a pump, the cited inlet flow may also be directed under pressure directly from chamber 24, for example a pressure chamber, into inlet 43 and may contain solely the flowable, e.g. liquid, medium. Shell 21 bounds an inner space open throughout. This space forms the reception 62 for reservoir 7 when positionally secured in support 63. Shells 21, 26 are longer than shell 36. Shell 37 is the longest of all shells of the dispenser.

Reference is made to U.S. Pat. No. 6,367,473 and to allowed U.S. pat. appl. Ser. No. 09/351,711 for incorporating the features and effects of the present invention. The size relationships as shown are particularly favorable. The properties and effects may be provided precisely or merely substantially or roughly the same as described and may also differ greatly therefrom depending on the requirements.

What is claimed is:

1. A dispenser capable of dispensing media, the dispenser comprising:
   two units (2, 3) and base bodies (4, 5), namely a first unit (2) including a first base body (4) and a second unit (3) including a second base body (5) displaceable relative to said first unit (2) from a resting position via a working stroke to an end position;
   a support (63) for at least one reservoir (7) substantially sealingly accommodating a discharge dose of the medium;
   an outlet duct (8), a medium outlet (9) and passages (55) for an inlet flow, and
   said base bodies (4, 5) including three housing shells (21, 26, 36) including two guide shells (21, 26), namely an inner and an outer guide shell, and a runner shell (36), said two guide shells (21, 26) being located bilaterally of said runner shell (36) and displaceable relative to said guide shells (21, 26), at least one of said housing shell (21, 26, 36) substantially enveloping said support (63), wherein both said two guide shells (21, 26) are located closely adjacent to said runner shell (36), and further defining a wall thickness of said runner shell (36) and a spacing between said guide shells (21, 26), wherein said wall thickness is in a range from greater than half of said spacing to twice said spacing.

2. The dispenser according to claim 1, wherein said runner shell (36) operationally substantially permanently envelopes said support (63).

3. The dispenser according to claim 1, wherein at least one of said guide shells (21, 26) is longer than said runner shell (36), said runner shell (36) being a single runner shell (36) and a single-walled runner shell (36) engaging between said two guide shells (21, 26).

4. The dispenser according to claim 1, further defining remote circumferential faces of said two guide shells (21, 26), wherein a catch is included and includes catch members (47, 48) located between said circumferential faces, said catch interlocking said two units (2, 3).

5. The dispenser according to claim 1 and further including a catch including catch members (47, 48), wherein said catch members (47, 48) are provided on an inner circumference of said outer guide shell (26) and on said runner shell (36).

6. The dispenser according to claim 1 and further including a catch including members (47, 48), wherein one of said housing shells (26) includes a recess (46) in a vicinity of said catch members (47, 48) for permitting said catch members (47, 48) to interengage.

7. The dispenser according to claim 1, further including means for preventing mutual withdrawal of said units (2, 3) under an axial withdrawal force, wherein said preventing means permit said mutual withdrawal by a force higher than said axial withdrawal force without destruction.

8. The dispenser according to claim 7, wherein said second unit (3) is rotatable relative to said first unit (2) to achieve first and second rotary positions, in said first rotary position said preventing means locking against said mutual withdrawal by said axial withdrawal force, in said second rotary position said preventing means permitting said mutual withdrawal by said axial withdrawal force.

9. The dispenser according to claim 1 and further including a transverse lug (53), wherein said transverse lug (53) protrudes radially outwardly beyond said runner shell (36).

10. The dispenser according to claim 1 and further including an end wall (27) included with said first base body (4), wherein at least one of said guide shells (21, 26) freely protrudes from said end wall (27), said guide shells (21, 26) and said end wall (27) commonly extending over substantially a full length of said first base body (49).

11. A dispenser capable of dispensing media, the dispenser comprising:
   two units (2, 3) and base bodies (4, 5), namely a first unit (2) including a first base body (4) and a second unit (3) including a second base body (5) displaceable relative to said first unit (2) from a resting position via a working stroke to an end position;
   a support (63) for at least one reservoir (7) substantially sealingly accommodating a discharge dose of the medium;
   an outlet duct (8), a medium outlet (9) and passages (55) for an inlet flow, and
   said base bodies (4, 5) including three housing shells (21, 26, 36) including two guide shells (21, 26), namely an inner and an outer guide shell, and a runner shell (36), said two guide shells (21, 26) being located bilaterally of said runner shell (36) and displaceable relative to said guide shells (21, 26), at least one of said housing shell (21, 26, 36) substantially enveloping said support (63), wherein both said two guide shells (21, 26) are located closely adjacent to said runner shell (36), further including means for preventing mutual withdrawal of said units (2, 3) under an axial withdrawal force, wherein said preventing means permit said mutual withdrawal by a force higher than said axial withdrawal force without destruction, said second unit (3) being rotatable relative to said first unit (2) to achieve first and second rotary positions, in said first rotary position said preventing means locking against said mutual withdrawal by said axial withdrawal force, in said second rotary position said preventing means permitting said mutual withdrawal by said axial withdrawal force, said preventing means including stops (47) and a counter stop (48) extending over an arc angle around said housing shells (21, 26, 36), said stops (47) being interspaced by arc spacings, namely an inner arc spacing between opposed flanks of said stops (47) and an outer arc spacing between remote flanks of said stops (47), said arc angle being bigger than at least one of said arc spacings.

12. A dispenser capable of dispending media, the dispenser comprising:

two units (2, 3) and base bodies (4, 5), namely a first unit (2) including a first base body (4) and a second unit (3) including a second base body (5) displaceable relative to said first unit (2) from a resting position via a working stroke to an end position;

a support (63) for at least one reservoir (7) substantially sealingly accommodating a discharge dose of the medium;

an outlet duct (8), a medium outlet (9) and passages (55) for an inlet flow, and said base bodies (4, 5) including three housing shells (21, 26, 36) including two guide shells (21, 26), namely an inner and an outer guide shell, and a runner shell (36), said two guide shells (21, 26) being located bilaterally of said runner shell (36) and displaceable relative to said guide shells (21, 26), at least one of said housing shell (21, 26, 36) substantially enveloping said support (63), wherein both said two guide shells (21, 26) are located closely adjacent to said runner shell (36), including a transverse lug (53), wherein said transverse lug (53) protrudes radially outwardly beyond said runner shell (36), and further defining an axis (10) for at least one of said housing shells (21, 26, 36) and a partial circumference of said runner shell (36), wherein said transverse lug (53) connects to said runner shell (36) only over said partial circumference and tangentially.

13. The dispenser according to claim 12 and further including a snap connection including a first snap member (47) and a second snap member (48) abutting on said first snap member (47), wherein said first and second snap members (47, 48) abut said first unit (2) relative to said second unit (3), said first and second snap members (47, 48) being resiliently displaceable.

14. The dispenser according to claim 13 and further defining remote ends of said guide shells (21, 26), wherein said first snap member (47) is supported on said first unit (2), said first snap member (47) being located between and spaced from said remote ends.

15. A dispenser for availing media comprising:

two units (2, 3) and base bodies (4, 5), namely a first unit (2) including a first base body (4) and a second unit (3) including a second base body (5) displaceable relative to said first unit (2) from a resting position via a working stroke to an end position;

a support (63) for at least one reservoir (7) substantially sealingly accommodating a discharge dose of the medium;

an outlet duct (8), a medium outlet (9) and passages (55) for an inlet flow, and said base bodies (4, 5) including three housing shells (21, 26, 36) including two guide shells (21, 26), namely an inner and an outer guide shell, and a runner shell (36), said two guide shells (21, 26) being located bilaterally of said runner shell (36) and displaceable relative to said guide shells (21, 26), at least one of said housing shell (21, 26, 36) substantially enveloping said support (63), wherein both said two guide shells (21, 26) are located closely adjacent to said runner shell (36), further including an end wall (27) included with said first base body (4), wherein at least one of said guide shells (21, 26) freely protrudes from said end wall (27), said guide shells (21, 26) and said end wall (27) commonly extending over substantially a full length of said first base body (49), and further including an actuating handle (29) and an outer face of said end wall (27), wherein said outer face includes at least one of said actuating handle (29), and a depression.

16. The dispenser according to claim 15 and further defining an outer circumferential face of said inner guide shell (21), wherein said support (63) is located within said outer circumferential face.

17. The dispenser according to claim 16 and further defining an inner circumferential face of said inner guide shell, wherein said support (63) is limited by said inner circumferential face.

18. The dispenser according to claim 15 and further defining a free end of said outer guide shell (26), wherein said support (63) axial protrudes beyond said free end.

19. A dispenser capable of dispensing media, the dispenser comprising:

two units (2, 3) and base bodies (4, 5), namely a first unit (2) including a first base body (4) and a second unit (3) including a second base body (5) displaceable relative to said first unit (2) from a resting position via a working stroke to an end position;

a support (63) for at least one reservoir (7) substantially sealingly accommodating a discharge dose of the medium;

an outlet duct (8), a medium outlet (9) and passages (55) for an inlet flow, and said base bodies (4, 5) including three housing shells (21, 26, 36) including two guide shells (21, 26), namely an inner and an outer guide shell, and a runner shell (36), said two guide shells (21, 26) being located bilaterally of said runner shell (36) and displaceable relative to said guide shells (21, 26), at least one of said housing shell (21, 26, 36) substantially enveloping said support (63), wherein both said two guide shells (21, 26) are located closely adjacent to said runner shell (36)

and further including a shield jacket (32), wherein said shield jacket (32) surrounds least one of said outer guide shell (26), and said runner shell (36).

20. The dispenser according to claim 19, wherein said second unit (3) includes said shield jacket (32), said shield jacket (32) extending over less than 360° and circumferentially translating into said runner jacket (36), said shield shell (32) being shorter than said runner jacket (36) and abutting on said guide shell (26) in said end position, said second base body (5) including an end wall (33) interconnecting said shield shell (32) and said runner shell (36), said end wall (33) including an actuating handle (35) of said second unit (3).

21. A dispenser capable of dispensing media, the dispenser comprising:

two units (2, 3) and base bodies (4, 5), namely a first unit (2) including a first base body (4) and a second unit (3) including a second base body (5) displaceable relative to said first unit (2) from a resting position via a working stroke to an end position;

a support (63) for at least one reservoir (7) substantially sealingly accommodating a discharge dose of the medium;

an outlet duct (8), a medium outlet (9) and passages (55) for an inlet flow, and said base bodies (4, 5) including three housing shells (21, 26, 36) including two guide shells (21, 26), namely an inner and an outer guide shell, and a runner shell (36), said two guide shells (21, 26) being located bilaterally of said runner shell (36) and displaceable relative to said guide shells (21, 26), at least one of said housing shell (21, 26, 36) substantially enveloping said support (63), wherein both said two guide shells (21, 26) are located closely adjacent to said runner shell (36)

and further including blocking means (49) for positively preventing said units (2, 3) from being transferred to said end position, wherein said blocking means (49) are manually releasable.

22. The dispenser according to claim 21, wherein said blocking means (49) include a locking member (52) for blockingly engaging an end face of said outer guide shell (26), said locking member (52) being located radially outside of said runner shell (36) and pivotably connecting to a shield jacket (32) included in a transverse lug (53), said locking member (52) being provided only along a flank of said transverse lug (53).

23. The dispenser according to claim 21, wherein said second unit (3) includes said medium outlet (9), at least one of said units (2, 3) being substantially axially symmetrical when in said end position.

24. The dispenser according to claim 21, wherein said second unit (3) includes a spike (37) for opening a reservoir closure (16) of said reservoir (7), said first and second units (2, 3) commonly bounding said passages (55) for directing said inlet flow into said reservoir (7).

25. A dispenser capable of dispensing media, the dispenser comprising:

two units (2, 3) and base bodies (4, 5), namely a first unit (2) including a first base body (4) and a second unit (3) including a second base body (5) displaceable relative to said first unit (2) from a resting position via a working stroke to an end position;

a support (63) for at least one reservoir (7) substantially sealingly accommodating a discharge dose of the medium;

an outlet duct (8), a medium outlet (9) and passages (55) for an inlet flow, and said base bodies (4, 5) including three housing shells (21, 26, 36) including two guide shells (21, 26), namely an inner and an outer guide shell, and a runner shell (36), said two guide shells (21, 26) being located bilaterally of said runner shell (36) and displaceable relative to said guide shells (21, 26), at least one of said housing shell (21, 26, 36) substantially enveloping said support (63), wherein both said two guide shells (21, 26) are located closely adjacent to said runner shell (36), at least one of said two units (2, 3) and said base bodies (4, 5) being made in one part.

26. The dispenser according to claim 25 and further including an insertion stud (34), wherein said second base body (5) includes said insertion stud (34) freely protruding toward said medium outlet (9), said insertion stud (34) including nested stud shells (37, 38), namely an inner stud shell (37) and an outer stud shell (38) spacedly enveloping said inner stud shell (37), said outer stud shell (38) circumferentially entirely forming a substantially continuous continuation of said runner shell (36) enveloping said support (63), said reservoir (7) including a single sealed reservoir tray including exclusively said discharge dose.

27. The dispenser according to claim 25, wherein said media include pharmaceutical remedies including biological active substances.

28. The dispenser according to claim 27, wherein said active substances include at least one of peptides, proteins, and hormones, said active substances including powder.

29. The dispenser according to claim 25, wherein said media include pharmacokinetic adjuvants.

30. A dispenser capable for dispensing media, the dispenser comprising:

two units (2, 3) and base bodies (4, 5), namely a first unit (2) including a first base body (4) and a second unit (3) including a second base body (5) displaceable relative to said first unit (2) from a resting position via a working stroke to an end position;

a support (63) for at least one reservoir (7) substantially sealingly accommodating a discharge dose of the medium;

an outlet duct (8), a medium outlet (9) and passages (55) for an inlet flow, and said base bodies (4, 5) including three housing shells (21, 26, 36) including two guide shells (21, 26), namely an inner and an outer guide shell, and a runner shell (36), said two guide shells (21, 26) being located bilaterally of said runner shell (36) and displaceable relative to said guide shells (21, 26), at least one of said housing shell (21, 26, 36) substantially enveloping said support (63), wherein both said two guide shells (21, 26) are located closely adjacent to said runner shell (36), said media include pharmacokinetic adjuvants and said pharmacokinetic adjuvant comprises a Freund adjuvant.

31. The dispenser according to claim 30, wherein said pharmacokinetic adjuvant is added to a drug or antigen to amplify a response of a patient's immune system.

* * * * *